United States Patent [19]

Sasaki et al.

[11] Patent Number: 5,311,277
[45] Date of Patent: May 10, 1994

[54] ATOMIC ABSORPTION SPECTROSCOPIC ANALYTIC APPARATUS

[75] Inventors: Kikuo Sasaki, Uji; Hidehisa Nishigaki, Joyo, both of Japan

[73] Assignee: Shimadzu Corporation, Kyoto, Japan

[21] Appl. No.: 857,066

[22] Filed: Mar. 24, 1992

[30] Foreign Application Priority Data

Mar. 30, 1991 [JP] Japan .................................. 3-093515

[51] Int. Cl.⁵ .................... G01J 3/30; G01N 21/72; G01N 21/74
[52] U.S. Cl. ........................................ 356/312; 356/315
[58] Field of Search ................................ 356/312, 315

[56] References Cited

U.S. PATENT DOCUMENTS

| | | | |
|---|---|---|---|
| 4,312,591 | 1/1982 | Tomoff | 356/315 |
| 4,406,541 | 9/1983 | Tomoff et al. | 356/312 |
| 4,991,960 | 2/1991 | Huber et al. | 356/315 |

Primary Examiner—Vincent P. McGraw
Assistant Examiner—K. P. Hantis
Attorney, Agent, or Firm—William L. Klima

[57] ABSTRACT

A sample injector (32) with an upwardly opened sample receiving hole is connected to an atomizer (36) of a flame type atomizing means and on a burner chamber (7) a flameless type atomizing means is mounted ahead of a burner head (9). For distribution of the sample by an auto-sampler (40) it is so arranged that the nozzle is movable to the sample bottle of the auto-sampler (40) and the sample injector (32) or a sample injection hole (30) of the atomizing means placed at the measuring position. This arrangement enables injection of the sample into the atomizing means of either type by means of a common auto-sampler, this facilitating switching between the flame system and the flameless system.

8 Claims, 4 Drawing Sheets

ATOMIC ABSORPTION SPECTROSCOPIC ANALYTIC APPARATUS

BACKGROUND OF THE INVENTION

1. Field of the Invention

The present invention relates to an atomic absorption spectrophotometer and, more particularly, to an atomic absorption spectrophotometer with an arrangement for flame system-flameless system switching in the atomizing means.

2. Prior Art

As atomizing method in atomic absorption spectroscopic analysis there are known two alternatives of flame system in which atomizing is done by burning a sample in a burner and flameless system in which atomizing is done by flowing a high-amperage current through a graphite tube of an electric furnace. In order to enable switching of these two atomizing systems with a single atomic absorption spectro-photometer, Hidehisa Nishigaki, one of the present inventors, already proposed an atomic absorption spectro-photometer provided with switchable atomizing means of each system (See Japanese Laid-open Patent Publication No. 61-286737.)

The flame system with its low sensitivity is suited for analysis of samples high in concentration, while the flameless system with its high sensitivity is recommended for analysis of samples low in concentration. These two systems are different in sampling method. In the flame system the sample solution is sucked via tube into an atomizer. In the atomizer the sample solution is mixed with a fuel gas and a combustion improving gas, the mixture is led from a burner chamber to a burner head and there it is atomized in a flame. Since the sample is sucked into the burner chamber continuously, the quantity of the sample is required to be quite large. Meanwhile, in the flameless system a trace amount of the sample (several tens µl) is injected into a sample inlet tube made of graphite and the graphite tube is then heated to atomize the sample.

As measurement is made by the flame system, it sometimes occurs that the sensitivity attainable is insufficient depending on the sample's concentration. And, should it be the case, it is necessary to do another measurement by the flameless system. During measurement by the flameless system, it also occurs that the sample's concentration is so high that the limits represented by the analytical curve are exceeded. Should it be the case, it is necessary to do re-measurement with the sample diluted properly or do it later by the flame system.

When measurement is taken with the flame system and the flameless system being switched, immediate re-measurement with the same sample is infeasible even by switching the atomizing method in case of an atomic absorption spectrophotometer provided with atomizing means of the flame system and the flameless system for the sampling method is different for each type of atomizing means.

With the atomic absorption spectrophotometer, too, adoption of an auto-sampler for automatic injection of a sample is conceivable. It is, however, infeasible to use a common auto-sampler for both systems if a suction type of sampling method is adopted for the flame system and a sampling method in which a trace amount of sample is dripped is adopted for the flameless system.

SUMMARY OF THE INVENTION

It is a principal object of the present invention relating to an atomic absorption spectrophotometer provided with two atomizing means of flame and flameless systems respectively to make switching between the flame system and the flameless system still more easy by making feasible injection of the sample into either atomizing means by the use of a common auto-sampler.

According to the present invention, the flame type atomizing means and the flameless type atomizing means are made switchable and the latter is disposed ahead of the burner head of the flame type atomizing means (i.e. on the side the operator is positioned) to facilitate use thereof, and at the same time make a common auto-sampler made usable in both atomizing means. For that a sample injector having an upwardly opening sample receiver for injection of the sample into the atomizing means of the flame system is connected to the atomizer and the auto-sampler is so disposed to enable injection of the sample into both of the sample injector of the flame system and the sample injection hole of the flameless system.

If it should be the case that the sample's concentration is too low and determination is infeasible during automatic analysis by the flame system by using an auto-sampler, the auto-sampler is used for injection of the sample into the graphite tube of the flameless system with the flameless type atomizing means moved to the measuring position for high sensitivity analysis.

Inversely, should it be the case that the sample's concentration is found too high during measurement by the flameless system, the atomizing means of the flame system is moved to the measuring position for the sample to be injected into the atomizing means of the flame system.

According to the present invention, the atomizing means of the flame system and of the flameless system can be switched as necessary and, if the sample to be measured next is low in concentration switching is done to the flameless system and vice versa and moreover a common auto-sampler can be used for efficient measurement of samples in a wide range of concentration.

The foregoing and other objects, features, aspects and advantages of the present invention will be become more apparent from the following detailed description of the present invention when taken in conjunction with the accompanying drawings.

DETAILED DESCRIPTION OF THE PREFERRED EMBODIMENT

Figure 1:
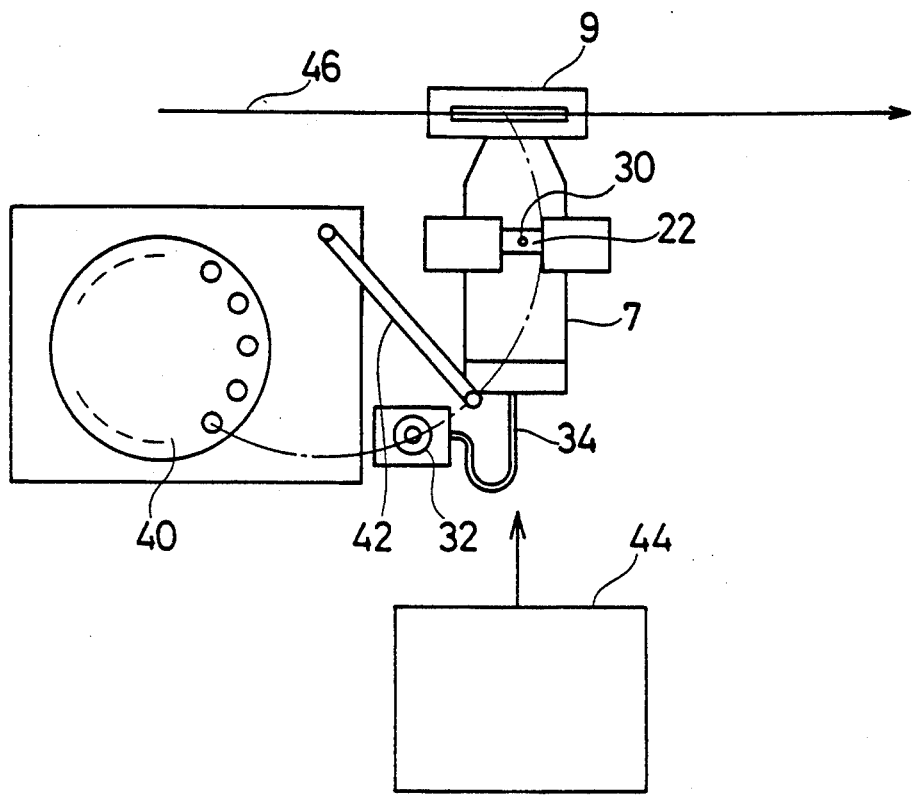
FIG. 1 is a schematic plan view showing an embodiment of the invention.
Figure 2:
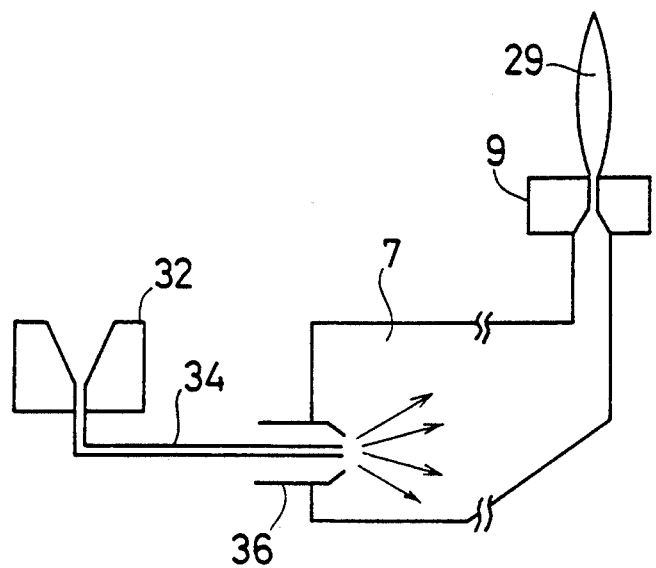
FIG. 2 is a schematic vertical section showing a flame type atomizing means.

FIG. 1 is a schematic plan view showing an embodiment of the invention and FIG. 2 is a schematic view showing the flame type atomizing means of the same embodiment.

It is assumed that, as shown in FIG. 1, the flame type atomizing means is placed at the measuring position. That is, the flame type atomizing means is so positioned that an optical axis 46 passes through the flame in a burner head 9. A sample injector 32 is connected via a flexible tube 34 of polytetrafluoroethylene to an atomizer 36 of a burner chamber 7 of the flame type atomizing means. The position of the sample injector 32 is fixed and the tube 34 has its length enough so that the fixed sample injector 32 need not be moved even when the burner chamber 7 is moved upward in FIG. 1 as the flameless type atomizing means is moved to the measuring position. The sample injector 32 is for microsampling and is funnel-shaped with its sample receiver opening upward.

The flameless type atomizing means is installed ahead of the burner head 9 on the burner chamber 7 (The operator stands below in FIG. 1 and the operator's side is called "ahead"). A numeral 22 denotes an electric furnace of the flameless type atomizing means comprising a graphite tube, being energized to be heated, and holds holding it on both sides. The graphite tube has therein a sample injection hole 30.

An auto-sampler 40 is equipped near both atomizing means, there is disposed an arm 42 with a nozzle attached at its tip for sucking and discharging the sample into the sample injector 32 or the sample injection hole 30 to properly distribute the sample put on the auto-sampler 40, and the nozzle attached to the arm 42 is moved as it swings between the sample containers on the auto-sampler 40, the sample injector 32 and the sample injection hole 30. As the flameless type atomizing means is placed at the measuring position, the sample injection hole 30 moves to a predetermined position on the optical axis 46.

There is provided a drive means 44 for automatically and selectively placing the flame type atomizing means and the flameless type atomizing means at the predetermined position on the optical axis 46. The drive means 44 comprises a moving mechanism for moving both linked atomizing means in vertical and longitudinal directions respectively and a pulse motor as driver.

Since, as shown in FIG. 1, the flameless type atomizing unit is placed ahead of the burner head 9, there is no risk of the burner head 9 obstructing the graphite tube changing work, the positioning precision of the sample injection hole 30 in the graphite tube and, moreover, the graphite tube can be set safely for immediately starting flameless type measurement even when the burner head 9 is quite hot just after completion of flame type measurement. The burner head 9 is still hot even more than 30 minutes after completion of measurement and there is a risk of suffering a burn if it is touched by bare hand. Thus, by placing the flameless type atomizing means ahead of the burner head 9, the flame type and the flameless type measurement can be done freely, securely and safely. Another merit of this arrangement is that safe sampling is ensured for there is no risk of the arm 42 moving above flame when an auto-sampler is used.

When a low-concentration sample has arrived during measurement by the flame system as shown in FIG. 1, switching to the flameless type measurement is feasible by moving the linked atomizing means upward as seen in the figure so that the optical axis passes through the flameless type atomizing means and then injecting the sample by the nozzle of the arm 42 through the sample injecting hole 30 of the flameless type atomizing means.

Inversely, when, for example, a high-concentration sample has arrived during measurement by the flameless system, switching to the flame type measurement is feasible by moving the linked atomizing means downward as seen in the figure so that the optical axis passes through the flame and then injecting the sample by the nozzle of the arm 42 from the auto-sampler 40 into the sample injector 32 of the flame type atomizing means.

In this embodiment the sample can be injected into the atomizing means at the measuring position no matter whether it is of the flame type or the flameless type.

Figure 3:
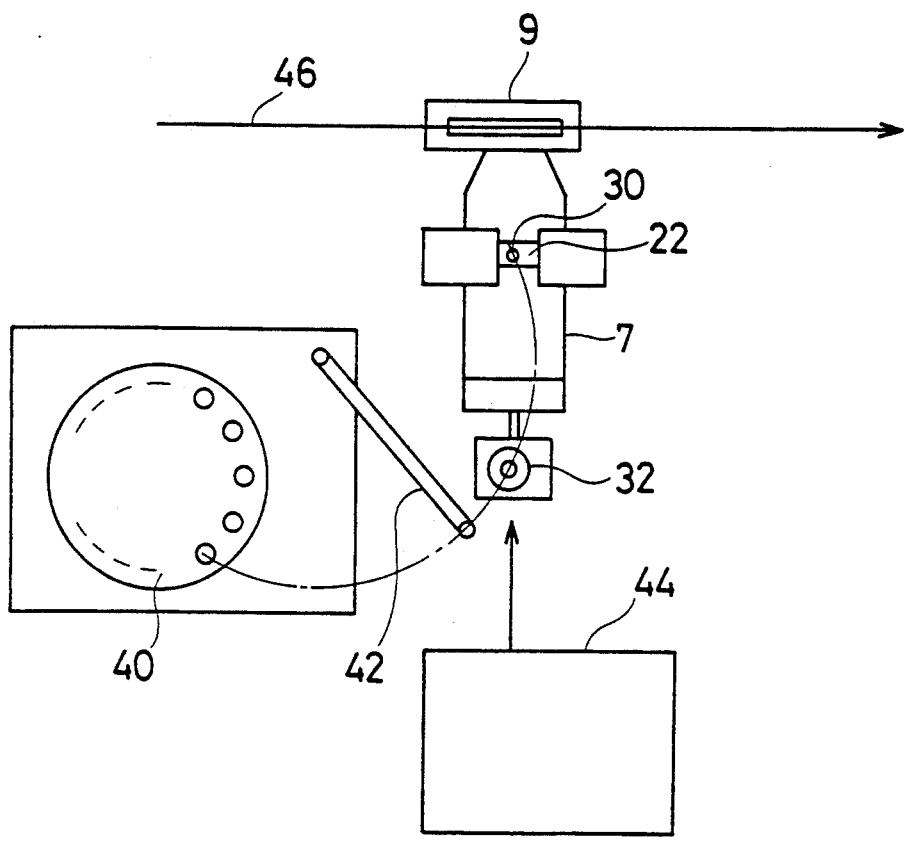
FIG. 3 is a schematic plan view showing another embodiment of the invention.

FIG. 3 shows a second embodiment.

In this embodiment it is so arranged that the sample injector 32 moves with the burner chamber 7 and the sample can be injected into the atomizing means of both flame type and flameless type when the former is at the measuring position. When the flameless type atomizing means is at the measuring position, the sample cannot be injected into the atomizing means of either type.

In the embodiment of FIG. 3 sample injection is feasible with the flame type atomizing means placed at the measuring position, when the flame type atomizing means is used for measurement but when flameless type atomizing means is used, the sample is injected with the flameless type atomizing means once moved off the optical axis 46 as shown in FIG. 3 and then the flameless type atomizing means is returned to the predetermined position on the optical axis 46 to be used for measurement.

Figure 4:
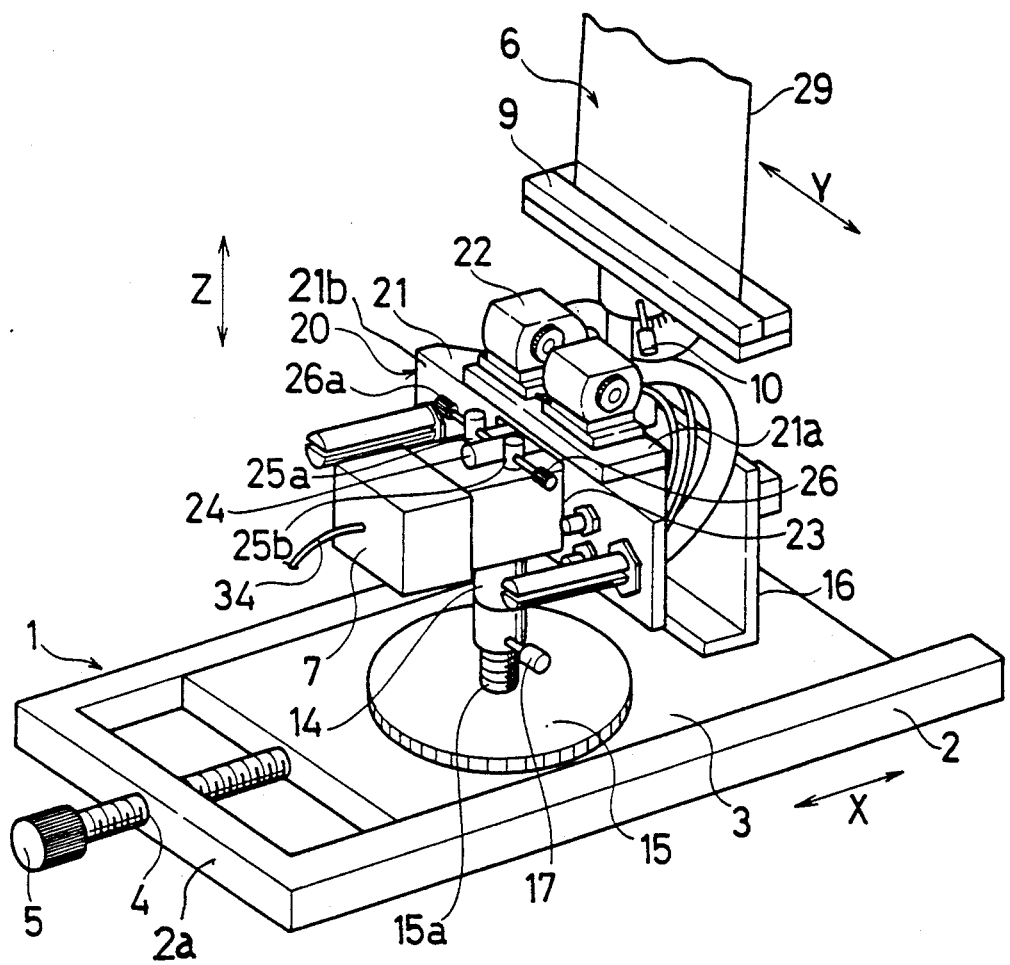
FIG. 4 is a perspective view showing the atomizing means of an embodiment of the invention.
Figure 5:
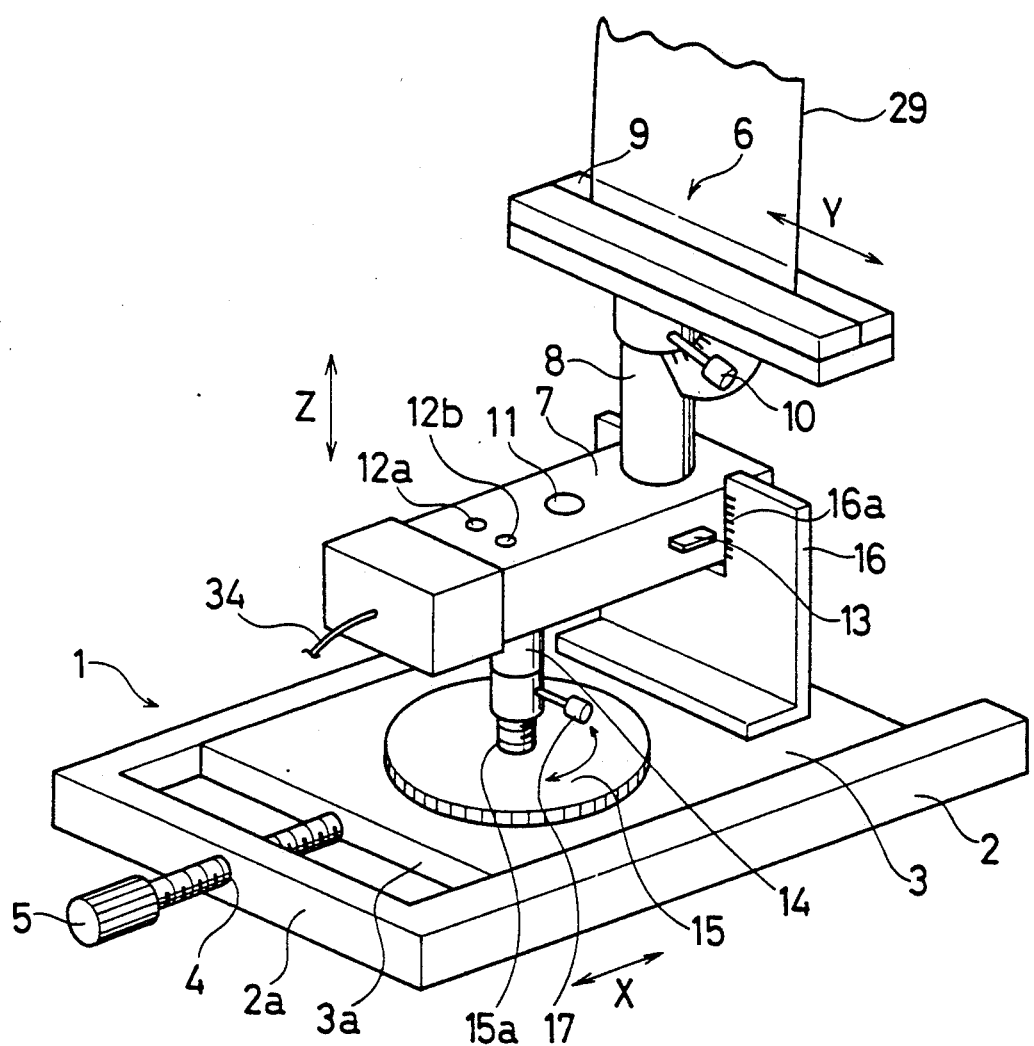
FIG. 5 is another perspective view of the embodiment of FIG. 4 with the flameless type atomizing means removed.

FIGS. 4 and 5 show an example in which switching of the types of atomizing means is done manually, not automatically. The embodiment of FIGS. 4 and 5 is already proposed by Nishigaki, one of the present inventors, and is described in Japanese Laid-Open Patent Publication No. 61-286737. FIG. 4 is a perspective view of the atomizing means and FIG. 5 is another perspective view of the same with flameless type atomizing means removed.

A support bed 1 is made up of a holding frame 2 and a movable plate 3 set therein to be freely slidable in the longitudinal direction (X-direction). A front member 2a of the holding frame 2 has set therethrough longitudinally a female screw 4 in which an adjusting screw 5 has screwed, and the inner end of the adjusting screw 5 is in contact with the front edge 3a of the movable plate 3 to be freely rotatable. Hence, the movable plate 3 set in the holding frame has its position adjustable along the side members thereof by rotating the adjusting screw 5.

The flame type atomizing means 6 is made up of the burner head 9 connected to the rear end portion of the burner chamber 7 via a cylinder 8. The burner head 9 has its extent of rotation about its axis finely adjustable with respect to the cylinder 8 and a screw 10 is provided for preventing rotation of the cylinder 8 after fine adjustment. At the top center of the burner chamber 7 there is provided a shaft-receiving hole 11 and along the front edge of the top side two screw receiver accommodating tapped holes 12a, 12b are provided. Near the rear end of one lateral side there is provided a dial holding piece 13 projecting sideways, and in the underside of the burner chamber projecting downward is a rotary shaft and inside this rotary shaft 14 there is formed a female screw opening downward (not shown).

About the center of the movable plate 3 the height adjusting screw 15 is provided freely rotatable about the perpendicular axis. Near the rear edge of the movable plate 3 a rotation stopper 16 is provided erect and in the upper portion thereof a notch 16a corresponding to the crosssection of the burner chamber 7. A male screw 15a of the height adjusting screw 15 is coupled with the female screw of the rotary shaft 14 with the rear end portion of the burner chamber 7 of the atomizing means 6 fitted in the notch 16a of the rotation stopper. When the height adjusting screw 15 is rotated in this condition, the rotation of the atomizing means 6 is prevented by the rotation stopper 16 and with the direction of the flame 29 through which the optical flux passes kept substantially transverse (Y-direction), it is feasible to adjust the height of the atomizing means 6 by lifting or lowering it along Z-direction. In order to accurately set the direction in which the optical flux passes the flame 29 transversely (Y-direction), the screw 10 may be loosened for adjustment to be made by rotating the burner head 9 about the cylinder 8 and, after adjustment, the screw 10 may be retightened. Rotation of the height adjusting screw 15 may be stopped by tightening the screw 17 for stopping the rotary shaft 14 after due adjustment of the height of the atomizing means 6.

Meanwhile, a flameless type of atomizing means 20 has its casing 21 so formed that a plate 21a placed on top of it and a front wall 21b has an inverted L crosssection and there are mounted electric furnaces 22 with graphite tubes et cetera housed therein on the plate 21a. In the front wall 21b of the casing 21 there is formed a notch 23 larger in size than the crosssectional shape of the burner chamber 7. About the center of the underside of the top late 21a there is provided a rotary shaft (not shown) corresponding to the shaft receiving hole 11 and a piece for adjusting the extent of rotation is projected forward from about the center in the upper portion of the notch 23.

When the atomizing means 20 is to be attached to the other atomizing means 6, screw receivers 25a, 25b are screwed into the tapped holes 12a, 12b in the topside of the burner chamber 7 and then fine adjusting screws 26a, 26b are screwed into the screw receivers 25a, 25b respectively. Now the casing 21 is set astraddle of the burner chamber 7 with the burner chamber 7 fitting in the notch 23, the rotary shaft (not shown) projecting downward from the underside of the top plate 21a is set in the shaft receiving hole 11 formed in the topside of the burner chamber 7 to be freely rotatable and the forward end of a projected piece 24 for adjusting the extent of rotation is positioned between the fine adjusting screws 26a, 26b. The direction in which the optical flux passes through the electric furnaces 22 is then set to be substantially transverse (Y-direction). In this case, the direction of the electric furnace can be made accurately transverse (Y-direction) by rotating the casing 21 with the rotary shaft (not shown) projecting downward from the underside of the top plate 21a as fulcrum by means of the fine adjusting screws 26a 26b, i.e. by turning these screws with a projecting piece 24 for fine adjusting the extent of rotation therebetween.

For the flame type measurement it is necessary to match the optical axis of the light source with that of the flame 29, while for flameless type of measurement it is necessary to match the optical axis of the light source with that of the electric furnace 22. For switching from the flame type measurement to the flameless type measurement, therefore, it is required to shift the optical axis of the electric furnace 22 to the position of the optical axis of the light source. For that, it is essential to move back the movable plate 3 by the necessary extent by means of the front and rear adjusting screw 5 and then also rotate the height adjusting screw 15 for lifting by the necessary extent. Switching from the flameless type measurement to the flame type measurement also can be carried out by a contrary proceeding with same manner as the above proceeding.

Although the present invention has been fully described by way of example with reference to the accompanying drawings, it is to be noted here that various changes and modifications will be apparent to those skilled in the art. Therefore, unless otherwise such changes and modifications depart from the scope of the present invention as defined by the appended claims, they should be construed as included therein.

What is claimed is:

1. An atomic absorption spectroscopic analytical apparatus, comprising:
   a flame type atomizing means provided with a burner head, said flame type atomizing means having an optical axis of a flame thereof set transversely relative to a direction of movement of said flame type atomizing means;
   a flameless type atomizing means placed ahead of said burner head and linked together with said flame type atomizing means, said flameless type atomizing means having an optical axis of an electric furnace thereof set parallel to said optical axis of said flame type atomizing means;
   a support bed for supporting said atomizing means linked together so as to be moveable together;
   a position adjusting mechanism for adjusting the position of said atomizing means linked together in both vertical and horizontal directions;
   a sample injector with a sample receiving hole opening upwardly connected to said flame type atomizing means; and
   an auto sample injecting mechanism capable of injecting a sample into said sample injector and a sample injecting hole of said flameless type atomizing means, said auto sample injecting mechanism including a pivoting arm moving through an arc and having a nozzle at its forward end for suction and discharge of the sample, said auto sampling injecting mechanism having a sample container fixed on a locus of said nozzle, and said sample receiving hole of said sample injector and said sample injecting hole of said flameless type atomizing means being positionable on said locus for receiving the sample.

2. An atomic absorption spectroscopic analytical apparatus according to claim 1, wherein said sample injector has its sample receiving hole fixed on the locus of said nozzle and connected with said atomizer via a flexible tube of a length allowing movement of said atomizer.

3. An atomic absorption spectroscopic analytical apparatus according to claim 1, wherein said sample injector is fixed to said atomizer so that it is positioned on the locus of said nozzle when said flame type atomizing means is placed at the measuring position.

4. An atomic absorption spectroscopic analytical apparatus according to claim 2, wherein the positional relation between said flameless type atomizing means and said nozzle is fixed so that said sample injection hole of said flameless atomizing means is to be on the locus of said nozzle when said flameless type atomizing means is placed at the measuring position.

5. An atomic absorption spectroscopic analytical apparatus according to claim 2, wherein the positional relation between said flameless type atomizing means and said nozzle is fixed so that said sample injection hole of said flameless type atomizing means is to be on the locus of said nozzle when said flame type atomizing means is placed at the measuring position.

6. An atomic absorption spectroscopic analytical apparatus according to claim 1, wherein said position adjusting mechanism is provided with a moving mechanism driven by a pulse motor for automatic switching of said atomizing means at the measuring position.

7. An atomic absorption spectroscopic analytical apparatus according to claim 1, wherein said position adjusting mechanism is provided with a height adjusting screw mechanism for adjusting the height of said linked atomizing means supported by said support bed and a longitudinal adjusting screw mechanism for longitudinal adjustment of the position of said support bed for manual switching of said atomizing means at the measuring position.

8. An atomic absorption spectroscopic analytical apparatus, comprising:
 a moveable flame type atomizer having a sample injector with a sample receiving port;
 a moveable flameless type atomizer with a sample injecting hole, said flameless type atomizer linked to said flame type atomizer;
 means for selectively moving said atomizers to a position along an optical axis;
 an auto sample injecting device capable of selectively delivering a sample to said atomizers, said auto sample injecting device defined by a swinging arm moving through an arc and having a sample delivery nozzle mounted thereon for suction and discharge of the sample.

* * * * *